United States Patent [19]

Ward

[11] 4,077,411
[45] Mar. 7, 1978

[54] KERATOPLASTY DEVICE

[76] Inventor: Donald E. Ward, 11158 Danbury St., Arcadia, Calif. 91006

[21] Appl. No.: 674,081

[22] Filed: Apr. 6, 1976

Related U.S. Application Data

[63] Continuation-in-part of Ser. No. 569,219, Apr. 18, 1975, abandoned.

[51] Int. Cl.$^2$ .............................................. A61B 17/00
[52] U.S. Cl. ................................. 128/303 R; 128/305; 128/346; 269/20
[58] Field of Search .................. 128/305, 346, 349 B, 128/303 R; 269/20; 51/235

[56] References Cited

U.S. PATENT DOCUMENTS

| | | | |
|---|---|---|---|
| 1,857,715 | 5/1932 | Falvo | 248/509 X |
| 2,598,060 | 5/1952 | Kadesky | 128/305 |
| 2,881,500 | 4/1959 | Furness | 128/346 UX |
| 2,929,603 | 3/1960 | Stewart | 128/346 X |
| 3,041,133 | 6/1962 | Hicks et al. | 269/20 X |
| 3,058,471 | 10/1962 | Shope | 128/305 |
| 3,134,208 | 5/1964 | Richmond | 51/235 |
| 3,459,175 | 8/1969 | Miller | 128/349 B UX |
| 3,488,674 | 1/1970 | Simjian | 269/20 X |

FOREIGN PATENT DOCUMENTS

| | | | |
|---|---|---|---|
| 842,400 | 7/1960 | United Kingdom | 248/505 |
| 926,072 | 5/1963 | United Kingdom | 269/20 |

Primary Examiner—Robert W. Michell
Assistant Examiner—Michael H. Thaler
Attorney, Agent, or Firm—Wm. Jacquet Gribble

[57] ABSTRACT

Apparatus for aiding eye corneal tissue transplant including a "Teflon" base with a flat platform and a central semispherical post to which a ring or rings are spring-loaded to secure the donated corneal tissue from storage. The post has a fitting for receiving a liquid injector such as a hypodermic syringe and the fitting connects to a vertical conduit in the post that discharges at the top of the post beneath the position of the donor tissue on the post. Before the tissue is secured to the post a biologically harmless liquid is introduced into the conduit from the syringe to part the tissue from the post and protect the delicate underside or endothelium layer of the corneal tissue during the trephining of the transplant "button" from the secured donor tissue.

7 Claims, 14 Drawing Figures

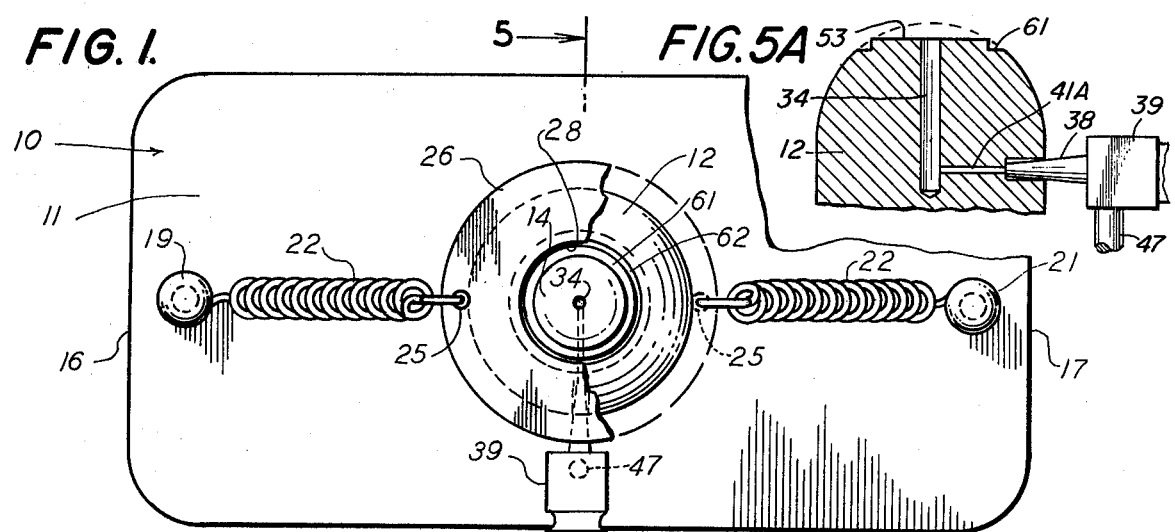
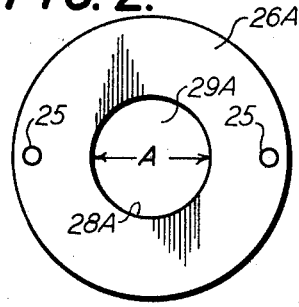
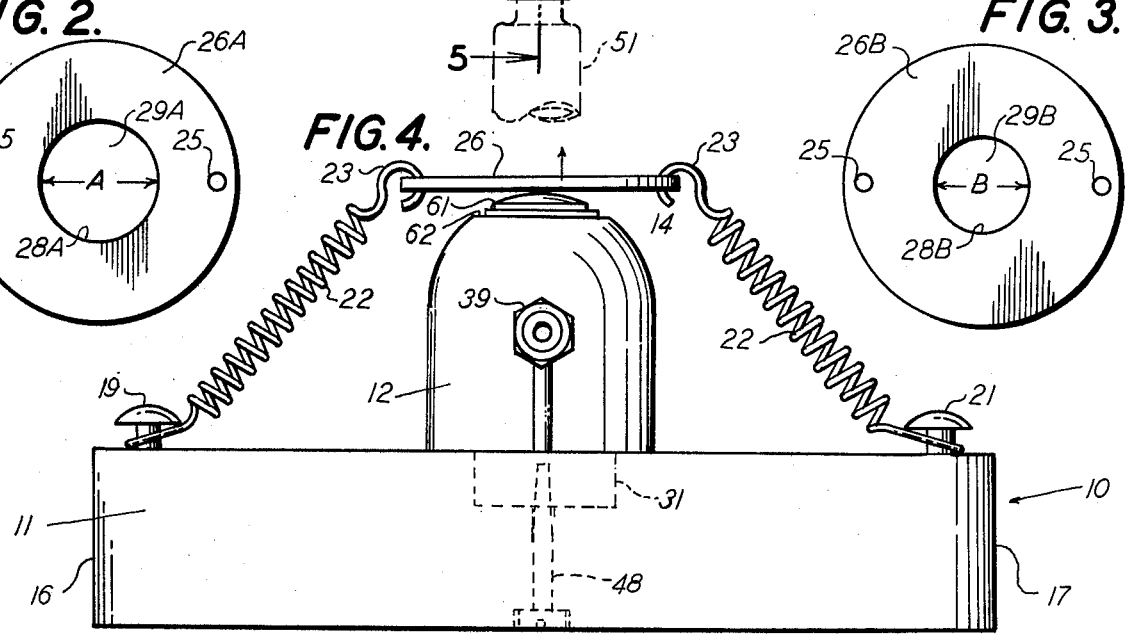
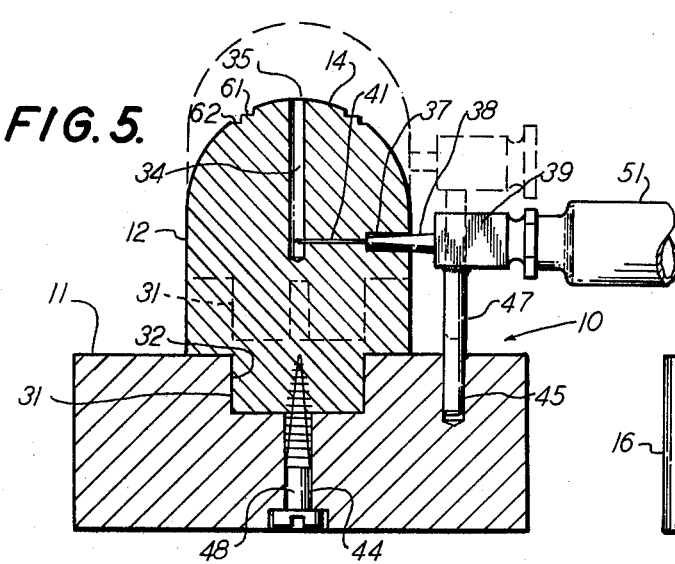
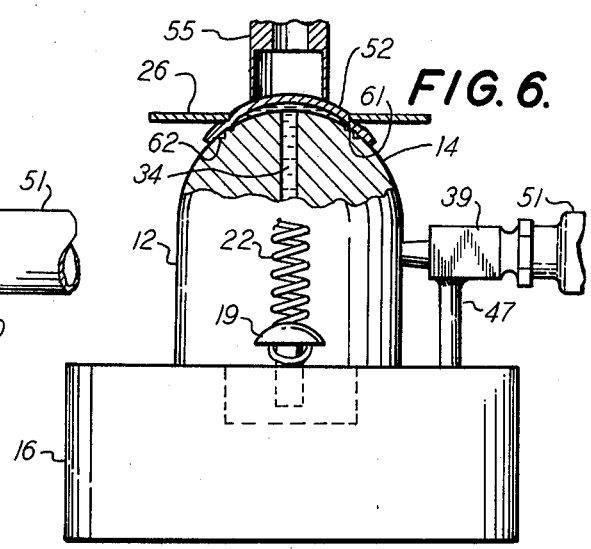

KERATOPLASTY DEVICE

This application is a continuation-in-part of application Ser. No. 569,219 filed Apr. 18, 1975 and having the same title, now abandoned.

BACKGROUND OF THE INVENTION

The invention relates to apparatus for implementing corneal transplants, or keratoplasty, and more particularly to method and apparatus for accomplishing the removal of the transplant button from separated and stored corneal tissue excised earlier from the eyeball of a donor. The general field of the invention is shown by the following U.S. Letters Patent:

Kendall U.S. Pat. No. 378,449 (Feb. 28, 1888);
Stewart U.S. Pat. No. 2,929,603 (Mar. 22, 1960)
and Swope U.S. Pat. No. 3,058,471 (Oct. 16, 1962).

Conventionally, the donor corneal tissue is stored as part of the whole eye in a moist chamber at 4° C. Such storage is possible only for twenty-four hours, within which time the recipient must be prepared for surgery to accept the corneal transplant button cut from the donor eye tissue using a trephine. The same trephine or one identical to it is used to remove the damaged corneal tissue from the recipient eye and the corneal transplant button is then sutured in place in the recipient eye. These surgical steps are normally accomplished under a microscope.

Newly developed storage methods for donor corneas enable the corneal tissue to be stored for much longer than 24 hours. Long-term and intermediate storage methods permit cornea storage for periods from one week to one year's time. The whole eye is not stored as previously, but just the corneal tissue which is separated from the sclera and the rest of the eye and stored in a container by itself. Storage is in the recipient's blood serum or in mineral oil at 4° C. Alternatively, it may be placed in a nutrient media and frozen with liquid nitrogen. More recent developments utilize a tissue culture media (such as McCarey-Kaufman corneal bathing Media) at 4° C to store the corneal tissue separated from the eye of the donor.

While long-term corneal tissue storage facilitates keratoplasty by being more adaptable to the recipient's needs in terms of health and timing, difficulties have prevented general use. For instance, competent surgeons have been reluctant to accept long-term stored corneal tissue as equal in quality to tissue obtained from the whole eye the day of separation from the donor body. Demonstrated success of keratoplasties using long-stored tissue has overcome this problem. Also, the conventional exacting surgical technique of trephining part way through the cornea while it is part of the donor eye and completing separation by scissoring an angle cut from the bottom of the trephine incision through the endothelium layer separating the cornea from the eye's anterior chamber, has not heretofore been practicable on corneal tissue removed from the eye. The endothelium, being a key to successful corneal transplant, must be protected from damage. Trephining the corneal button on stored separated tissue has therefore been done from the endothelium side against a support surface, precluding the preferred keratoplasty techniques, including preparation of an endothelium flap on the button to seal the recipient cornea aperture against leakage of the aqueous humor which is within the anterior chamber of the eye between the cornea and the iris. To operate with the endothelium layer against a work surface to achieve normal techniques harms that layer and thus inhibits effective transplant.

I have invented apparatus and process whereby separated corneal tissue stored for long periods of time, with the attendant advantages to the recipient of such storage, can be transplanted with accepted surgical techniques under a microscope without damage to the endothelium or other parts of the transplant button.

SUMMARY OF THE INVENTION

The invention contemplates apparatus for use with a liquid injector and comprising a work base with a work surface on the base and a liquid conduit in the base opening at the work surface. Means on the base are adapted to receive the liquid injector. The means on the base connects to the liquid conduit. Releasable securing means holds the corneal tissue to be transplanted to the base about the conduit discharge at the work surface, against the pressure of liquid introduced from the liquid injector.

The process of the invention contemplates the steps of forming a convex miniscus of liquid atop a work surface and releasably securing corneal transplant tissue to the surface over the liquid with the endothelium of the cornea spaced from the work surface by the liquid, protecting the delicate endothelium layer. The further steps include trephining through a portion of the thickness of the cornea while maintaining a liquid pressure on the endothelium layer and separating then a transplant button from the secured corneal tissue by making a sloping incision from the bottom of the trephine cut outwardly through the endothelium layer to define a sealing flap on the corneal transplant button in presently approved medical practice.

Preferably the means adapted to receive a liquid injector is a conventional hypodermic needle held in the work base and the liquid injector may therefore comprise a conventional hypodermic syringe which may be releasably attached conventionally to the means on the base for the introduction of fluid to the conduit, the liquid preferably being similar in qualities to the aqueous humor or to the nutrient media in which the tissue was stored, both these liquids being beneficial to the endothelium.

Since keratoplasty is performed in a sterile environment, it is preferred that the base be of Teflon or of other material that is easily cleaned and is chemically inert, in addition to being resistant to damage at autoclave temperatures. A preferred means for securing the corneal tissue to the work base is a semispherical work surface on the base with an annular land matching the inner diameter of a hold-down ring releasably biased toward the work surface to bind the corneal tissue or button source between the ring being used and the work base. The ring holds the tissue in place on the base and resists the pressure of the liquid separating the corneal tissue from the work surface at the area of trephining even though additional liquid increases pressure. By using a dark pigmented Teflon for the work base and a suitable mass of material to give the base solidity with respect to the microscope, the surgical procedure may be done with acute visual accuracy and stability.

These and other advantages of the inventive apparatus and process are apparent from the following detailed description and drawing.

BRIEF DESCRIPTION OF THE DRAWING

FIG. 1 is a plan view, partly broken away, of a keratoplasty device in accordance with the invention;

FIGS. 2 and 3 are plan views of hold-down rings for use with the device of FIG. 1;

FIG. 4 is a front elevation of the device of FIG. 1;

FIG. 5 is a sectional elevation taken along line 5 — 5 of FIG. 1;

FIG. 5A is a sectional elevation similar to FIG. 5 of an alternate embodiment of the invention;

FIG. 6 is an end elevation, partly in section, of the device of FIG. 1 illustrating the process of the invention;

DESCRIPTION OF THE PREFERRED EMBODIMENT

Figure 7:
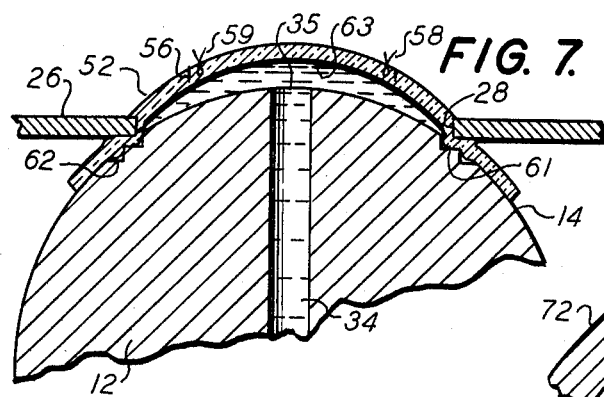
FIG. 7 is a enlarged fragmentary sectional elevation similar to FIG. 6 showing a further step of the process.

In the various figures like parts are referred to by like reference characters.

In FIGS. 1–5 the apparatus of the invention is shown. A support assembly 10 has a flat platform 11 of generally rectangular configuration, as seen in FIG. 1, and a cylindrical post 12 rising from platform 11 to a hemispherical work surface 14. Along the longitudinal axis of the platform near the ends 16, 17 thereof are roundhead fasteners like rivets 19, 21 to each of which one end of an extension spring 22 is secured. The springs may be stainless steel.

The other end of each extension spring passes through one of a pair of openings 26 diametrically opposed in a hold-down ring 26. The springs bias the ring, which has an annular wall 28 defining an inner aperture 29, toward hemispherical work surface 14. The hold-down ring is adapted to retain corneal tissue (not shown) on the work surface.

FIGS. 2 and 3 show hold-down rings 26A and 26B, respectively, which, like the springs, may be of stainless steel. Each has a pair of diametrically opposed rim holes 25 adapted to receive ends 23 of the springs. Ring 26A has an annular wall 28A with a diameter "A" while ring 26B has an annular wall 28B with a diameter "B". In practice the diameters best suited to the invention have been found to be: $A = 9/16$ inch and $B = \frac{1}{2}$ inch, respectively, in rings of 1¼ inches outside diameter. Preferably post and platform are of a dense inert plastic, such as "Teflon", with the platform being about 4 inches long. The post is preferably of a dark pigmented Teflon rod of 1 inch diameter and, as can be seen from FIG. 5, has a reduced diameter boss 31 that seats in an annular recess 32 in the center of the platform. Since the keratoplasty procedure is normally performed under a microscope in sterile conditions, a dense inert material, such as Teflon, has been found suitable both to withstand autoclaving and to have sufficient mass to be stable beneath the microscope.

The post has a central conduit 34 with an upper discharge orifice 35 in the center of the hemispherical work surface 14. A horizontal recess 37 in the side of the post receives a tapered needle holder 38 of a hypodermic needle fitting 39 from which a shortened needle 41 extends into fluid communication with conduit 34. Alternatively, a clear bore 41A, as shown in FIG. 5A, may replace needle 41 to reduce clogging.

In addition to the central annular recess 32, platform 11 has a central screw aperture 44 and a pin recess 45 in its upper surface adjacent the post. The pin recess receives a fitting pin 47 which is silver soldered or otherwise fixed to the needle fitting 39 prior to the assembly of the fitting with the post.

In assembling the support assembly 10 of FIG. 1, the needle fitting 39 is first assembled with the post by inserting the needle-holder 38 into horizontal recess 37 and then the post boss 31 and the pin 47 are lodged, respectively, in annular recess 32 and pin recess 45. A screw, such as a sheet metal screw 48, is then engaged with boss 31 of the post, as shown in FIG. 5, to fix the post to the platform and secure the needle fitting 39 with respect to the conduit 34 in the post.

Since it is desired to introduce fluid such as a nutrient or a neutral aqueous liquid between the semispherical work surface and the corneal tissue to be secured to the work surface, the needle fitting 39 is adapted to receive a liquid-filled hypodermic syringe, such as the syringe 51 shown fragmentarily in FIG. 5 and indicated in broken lines at 51 in FIG. 1. Depending upon the viscosity of the liquid, it may be desired to flat the top of surface 14 to maintain the liquid thereon in a convex miniscus as shown in an alternate embodiment in FIG. 5A. The flat 53 being circumscribed by an annular land 61 to aid the seating of the hold-down ring 26 as described later on.

In the process of the invention, which is illustrated in part in FIGS. 6 and 7, the support assembly 10 is removed from an autoclave or other sterilizer and placed on a work table in the field of a microscope (neither being shown). A free convex miniscus is carefully formed on work surface 14 from syringe 51. Corneal tissue is then removed from its storage container and hold-down ring 26 is displaced against the spring bias from its position at work surface 14. The tissue is then carefully placed on the convex miniscus of the liquid upon the work surface with the endothelium on the liquid and separated from the work surface by the liquid. In FIG. 6 the corneal tissue is indicated at 52. The hold-down ring is then carefully restored to position with the corneal tissue between the ring and the work surface. Further liquid may be introduced from syringe 51 to the space beneath the tissue to insure separation of the endothelium from the work surface during operative steps thereon.

With the hold-down ring in place and a liquid cushion protecting the endothelium layer against mechanical damage, the delicate trephining of the transplant button may begin. As indicated in FIG. 6, a schematically shown trephine 55 is applied to the exterior or epithelium of the corneal tissue near its center. With the downward pressure of the trephine being resisted by the liquid pressure induced by the hypodermic syringe, the liquid cushion at all times separates the endothelium from the work surface.

Turning now to FIG. 7, with the trephine removed, a circular incision approximately four-fifths the thickness of the cornea has been made by the trephine. The vertical incision is indicated at 56. With the trephine removed, stay sutures, such as the suture loops 58, 59 are stitched into the corneal tissue within the confines of the trephine incision to aid in manipulating the transplant button defined by the trephining, once the cutting is completed.

It has been found that the corneal tissue may be securely held by hold-down ring 26 if annular lands 61, 62 circumscribe the central area of the work surface. The lands are defined by 0.010 inch deep steps, although shown out of scale in the figures for better clarity. As can be seen from FIG. 7, the downward pressure of the ring 26 distorts the scleral tissue against the land commensurate in diameter with the ring aperture 29 so that the scleral tissue is securely held against the land, not only securing the tissue in place but also sealing the liquid within the space between the hemispherical work surface 14 and the endothelium layer 63, shown as a solid black arc in FIG. 7.

The advantages of the inventive apparatus and process are better understood with a knowledge of the conventional procedure for removing the corneal transplant button from the donor corneal tissue, a very critical part of the keratoplasty process. In FIGS. 8–13 a donor eyeball is fragmentarily shown diagrammatically. The well-known components of the eye are indicated in all of the figures as follows: the corneal tissue 71 rising from the curvature of the outer covering, or sclera 72, the sclera enclosing the inner eye with a lens 73 held by zonule 74 from the ciliary body 75 within the eye. The iris is indicated at 76 partially covering the lens and defining the pupil 77.

While the cornea 71 is known to comprise several layers such as the pavement epithelium, Bowman's membrane, the stroma and the endothelium over Descemet's membrane, only the endothelium is indicated in exaggerated thickness at 63 because of its importance to the success of the keratoplasty. Normally the endothelium is a single cell layer in contact with the aqueous humor of the eye in the anterior chamber thereof, and, since it is the nutrient absorbing layer for the cornea, its survival in the keratoplasty is critical to a successful corneal transplant.

Figure 8:
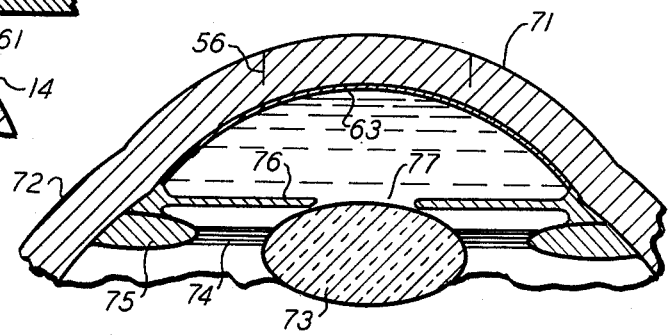
FIGS. 8–11 illustrate schematically the conventional surgical steps of keratoplasty in preparing the transplant button from the eyeball of a donor.
Figure 9:
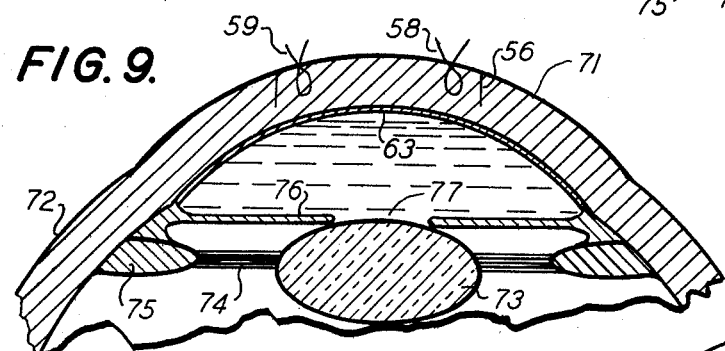

The technique shown in FIGS. 8–13, developed by competent surgeons, has as its objective precise sizing of the transplant button, creation of a sealing flap and the survival of a considerable endothelium area. Therefore, as shown in FIG. 8, the trephine incision indicated at 56 is made about four-fifths of the thickness of the cornea at its center. Stay suture loops 58, 59 are applied within the circle of the trephine incision as manipulative aids, the number of stay sutures depending upon the preference of the surgeon. Scissors are then used at an angle to incision 56 to incise a truncated conical section, indicated in FIG. 10 at 79, and shown separated in FIG. 11 from the donor eye, along with the rest of the transplant button 80. Note that the frusto-conical flap 79 includes the endothelium layer 63 and that the extent of the layer 63 is greater than the area of the rest of the transplant button.

Figure 12:
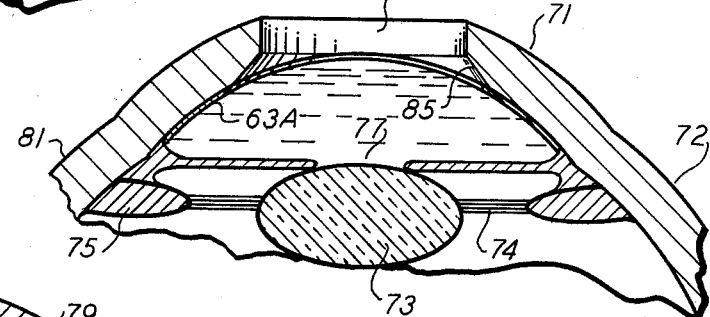
FIG. 12 shows schematically in section the prepared eyeball of the recipient.
Figure 10:
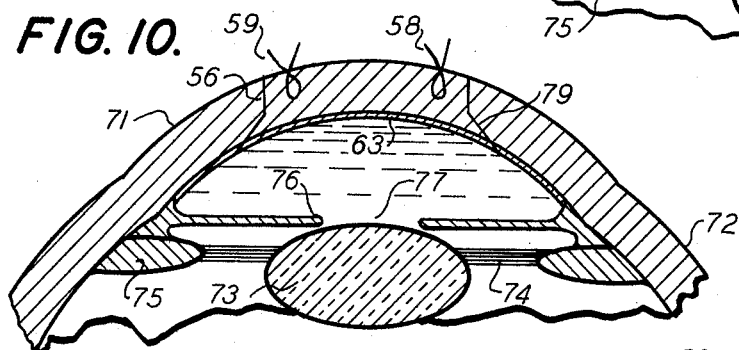
Figure 11:
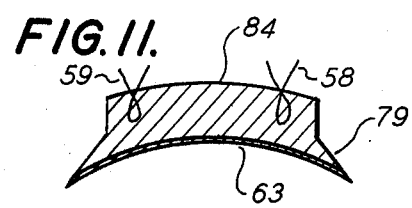
Figure 13:
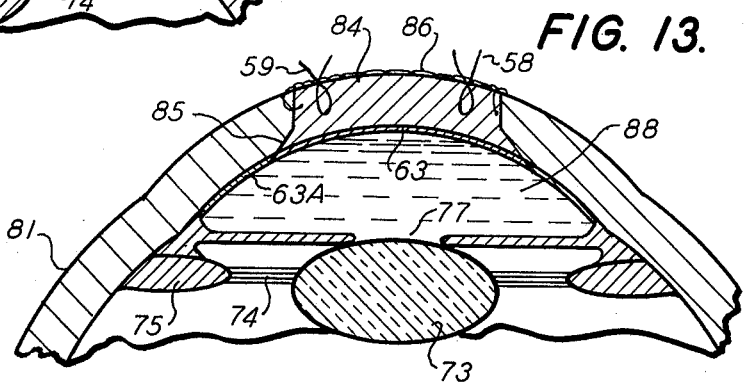
FIG. 13 is a fragmentary schematic sectional elevation of the eyeball of the recipient after receiving the corneal transplant.

In FIG. 12 a recipient's eye 81 is fragmentarily shown in diagram fashion with a trephined and scissored opening 82 exactly matching in diameter and depth the incision 56 of FIG. 8. Opening 82 has also been made under a microscope or other extreme magnification with trephine and surgical scissors incising all layers of the corneal tissue including the endothelium. In FIG. 13 corneal button 80 of FIG. 11 has been maneuvered carefully into place in the opening 82 of the recipient eye 81, chiefly by means of the stay sutures 58, 59 and the endothelium flap in its frustoconical configuration 79 is in close contact with the frustoconical cavity 85 of the recipient eye. The transplant button 80 is then precisely stitched in place with sutures 86 as indicated in FIG. 13. The transplanted endothelium layer 63 is in intimate contact with the aqueous humor 88 of the recipient eye and the frusto-conical flap 79 effectively seals the trephined and scissored cavity 82 against loss of the aqueous humor from the anterior chamber of the eye.

With the endothelium protected by the fluid cushion in the manner made possible by the inventive apparatus and process herein described, the corneal transplant button can be removed from the donor to the recipient eye and secured precisely in place without damage to the endothelium or other portions of the transplanted tissue. Surgeons acquainted with the previous technique in taking transplant buttons from the donor eye directly can readily practice their learned technique on carefully stored separated tissue by means of the inventive apparatus and process and benefit from the advantages of ready, convenient transplant material without sacrifice of any advantages of the medically proven keratoplasty procedures of the past.

Since modifications within the scope of the invention other than those shown and described herein may occur to those skilled in this particular art, it is desired that the invention be measured by the appended claims rather than by the purely illustrative description and drawing above disclosing the invention.

I claim:

1. Apparatus for corneal tissue keratoplasty for use with a liquid injector and comprising a work base, a work surface on the base adapted to retain a miniscus, a liquid conduit in the base opening at the work surface, means on the base adapted to receive a liquid injector, said means on the base connecting to the liquid conduit and said conduit discharging from the base, and means for securing tissue to the base about the conduit discharge at the work surface.

2. Apparatus in accordance with claim 1 wherein said work base comprises a flat platform, and a central post projecting from the platform.

3. Apparatus in accordance with claim 2 wherein said work surface comprises a partly spherical area on said central post remote from said flat platform, said liquid conduit emerging centrally of said partly spherical area.

4. Apparatus in accordance with claim 2 further comprising a flat area on the work surface surrounding the liquid conduit discharge.

5. Apparatus for use with a liquid injector for supporting eye corneal tissue for keratoplasty and comprising a base, a post fixed to the base, a hold-down ring having an inner diameter less than the diameter of the work surface, spring means biasing the ring toward the work surface, a liquid conduit in the post terminating in a liquid conduit discharge at the central portion of the work surface, a work surface flat adapted to retain a miniscus and surrounding the liquid conduit discharge, a hypodermic needle communicating with the conduit and adapted to receive a liquid injecting syringe to conduct liquid from said syringe to the conduit in the post, means securing the needle with respect to the post, and attachment means releasably securing the post and needle to the base.

6. Apparatus in accordance with claim 5 wherein said means securing the needle to the post comprises a horizontal recess in the post.

7. Apparatus in accordance with claim 5 wherein said attachment means comprises a pin fixed to the needle, a pin recess in the base, a post recess in the base, a reduced diameter boss on the post seated in the post recess, and a fastener in the base engaging the post.

* * * * *